United States Patent [19]

Chodorow et al.

[11] Patent Number: 5,458,579
[45] Date of Patent: Oct. 17, 1995

[54] MECHANICAL TROCAR INSERTION APPARATUS

[75] Inventors: Ingram S. Chodorow, Upper Saddle River; M. Zubair Mirza, Wyckoff, both of N.J.

[73] Assignee: Technalytics, Inc., Montvale, N.J.

[21] Appl. No.: 981,234

[22] Filed: Nov. 25, 1992

Related U.S. Application Data

[63] Continuation-in-part of Ser. No. 815,440, Dec. 31, 1991, and a continuation-in-part of Ser. No. 815,488, Dec. 31, 1991, and a continuation-in-part of Ser. No. 903,084, Jun. 17, 1992.

[51] Int. Cl.$^6$ .................................................. A61M 5/178
[52] U.S. Cl. .......................... 604/165; 604/280; 606/167; 606/170
[58] Field of Search .................................. 604/116, 177, 604/179, 180, 264, 280, 283; 606/130, 167, 170, 186, 185

[56] References Cited

U.S. PATENT DOCUMENTS

| 1,147,408 | 7/1915 | Kells . | |
| 1,213,001 | 1/1917 | Philips . | |
| 1,835,287 | 12/1931 | Donovan . | |
| 2,097,039 | 10/1937 | Peterson | 128/347 |
| 2,496,111 | 1/1950 | Turkel | 128/2 |
| 2,525,329 | 10/1950 | Wyzenbeek | 128/347 |
| 2,541,542 | 2/1951 | Perez et al. | 128/2 |
| 2,623,521 | 12/1952 | Shaw | 128/221 |
| 3,007,471 | 11/1961 | McClure, Jr. | 128/2 |
| 3,039,468 | 6/1962 | Price | 128/347 |
| 3,046,984 | 7/1962 | Eby | 128/DIG. 26 |
| 3,090,384 | 5/1963 | Baldwin et al. | 128/221 |
| 3,368,564 | 2/1968 | Selix | 128/DIG. 26 |
| 3,459,189 | 8/1969 | Alley et al. | 128/347 |
| 3,540,447 | 11/1970 | Howe | 128/221 |
| 3,545,443 | 12/1970 | Ansari | 128/214.4 |
| 3,565,074 | 2/1971 | Foti | 128/214.4 |
| 3,613,684 | 10/1971 | Sheridam | 128/348 |
| 3,752,161 | 8/1973 | Bent | 606/184 |
| 3,789,852 | 2/1974 | Kim et al. | 128/347 |
| 3,817,250 | 6/1974 | Weiss et al. | 128/305 |
| 3,835,860 | 9/1974 | Garretson | 606/184 |
| 3,860,006 | 1/1975 | Patel | 128/347 |
| 3,895,632 | 7/1975 | Plowiecki | 128/414 |
| 3,993,079 | 11/1976 | Gatztaëondo | 128/347 |
| 3,994,287 | 11/1976 | Turp et al. | 128/6 |
| 4,013,080 | 3/1977 | Froning | 128/347 |
| 4,134,399 | 1/1979 | Hylderson | 128/888 |
| 4,177,814 | 12/1979 | Knepshield et al. | 128/348 |
| 4,180,068 | 12/1979 | Jacobsen et al. | 128/214 |
| 4,186,750 | 2/1980 | Patel | 128/748 |
| 4,215,699 | 8/1980 | Patel | 128/748 |
| 4,254,762 | 3/1981 | Yoon | 128/4 |
| 4,299,230 | 11/1981 | Kubota | 128/630 |
| 4,345,589 | 8/1982 | Hiltebrandt | 128/4 |
| 4,470,410 | 9/1984 | Elliott | 128/877 |
| 4,516,968 | 5/1985 | Marshall | 128/DIG. 26 |
| 4,535,773 | 8/1985 | Yoon | 604/51 |
| 4,654,030 | 3/1987 | Moll et al. | 604/165 |
| 4,675,006 | 6/1987 | Hrushosky | 128/DIG. 26 |
| 4,755,173 | 7/1988 | Konopka | 128/DIG. 26 |
| 4,769,010 | 9/1988 | Finton | 128/DIF. 26 |
| 4,898,587 | 2/1990 | Mora | 604/180 |
| 4,902,280 | 2/1990 | Lander | 604/165 |
| 4,926,883 | 5/1990 | Strock | 128/888 |
| 4,982,842 | 1/1991 | Hollister | 206/365 |
| 5,066,288 | 11/1991 | Deniega . | |
| 5,073,169 | 12/1991 | Raiken | 604/180 |
| 5,176,648 | 1/1993 | Holmes et al. | 604/180 |
| 5,201,742 | 4/1993 | Hasson | 606/130 |

Primary Examiner—Randall L. Green
Assistant Examiner—Rob Clarke
Attorney, Agent, or Firm—Rosen, Dainow & Jacobs

[57] ABSTRACT

Apparatus for inserting a trocar/cannula assembly through a wall of an anatomical cavity of a patient, the apparatus including a housing for holding a trocar/cannula assembly, a spine having a longitudinal axis, the spine having proximal and terminal ends, the housing coupled to the spine for movement along said axis, holding means on the housing for holding a trocar/cannula assembly, and drive means coupled to said housing and spine for driving said housing axially on said spine toward said terminal end thereby moving said housing from an initial position to a final position, whereby the trocar/cannula assembly carried by said housing is moved axially along said spine.

22 Claims, 10 Drawing Sheets

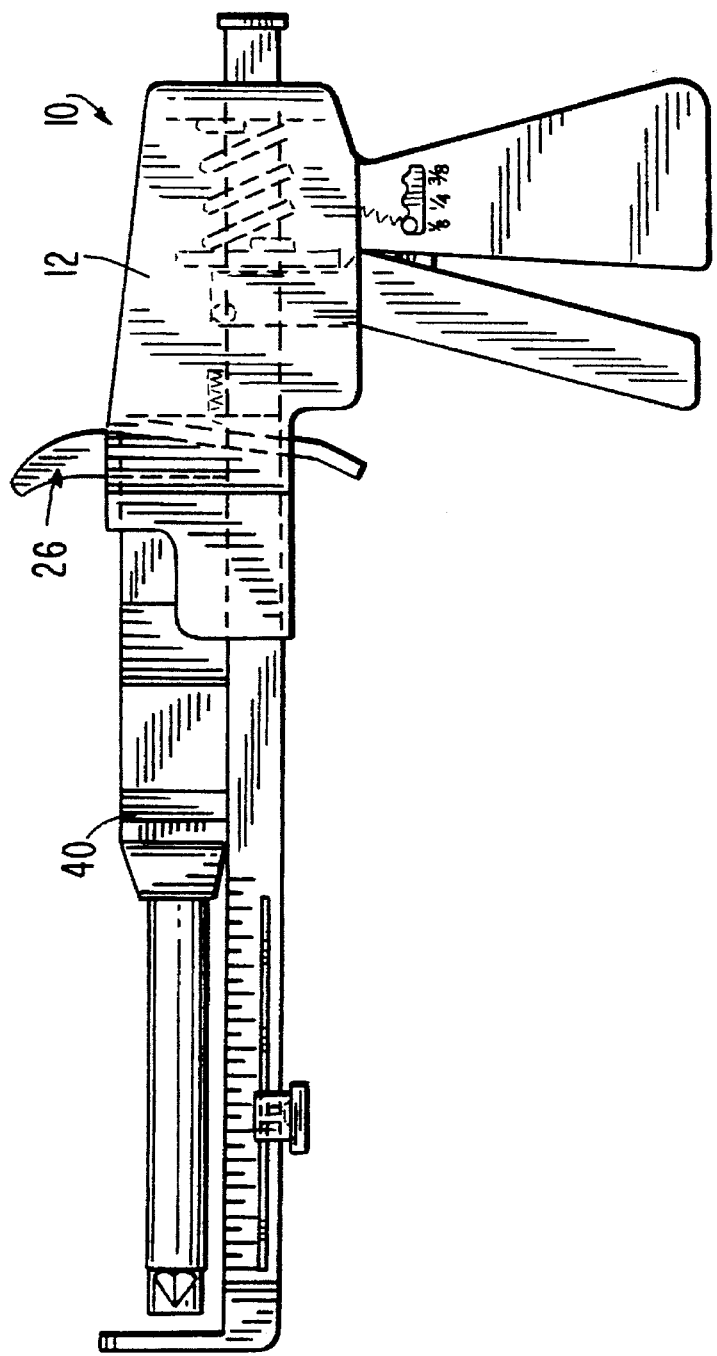
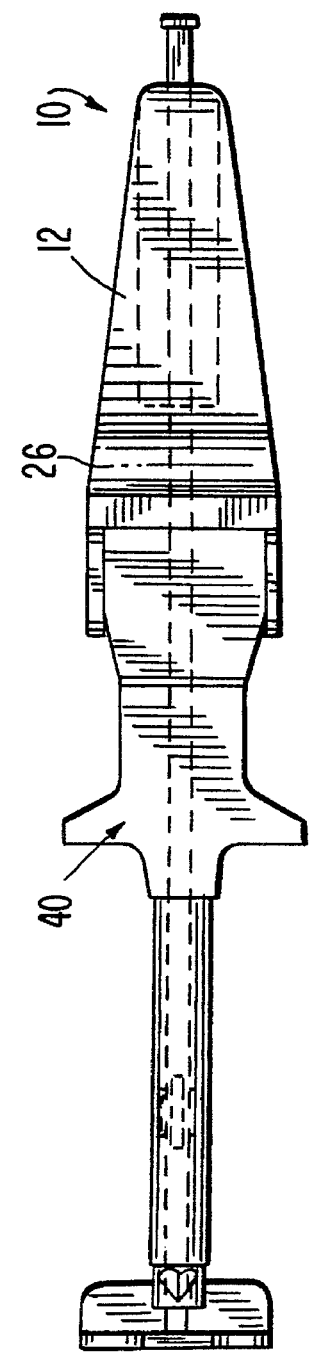
FIG.3
FIG.4

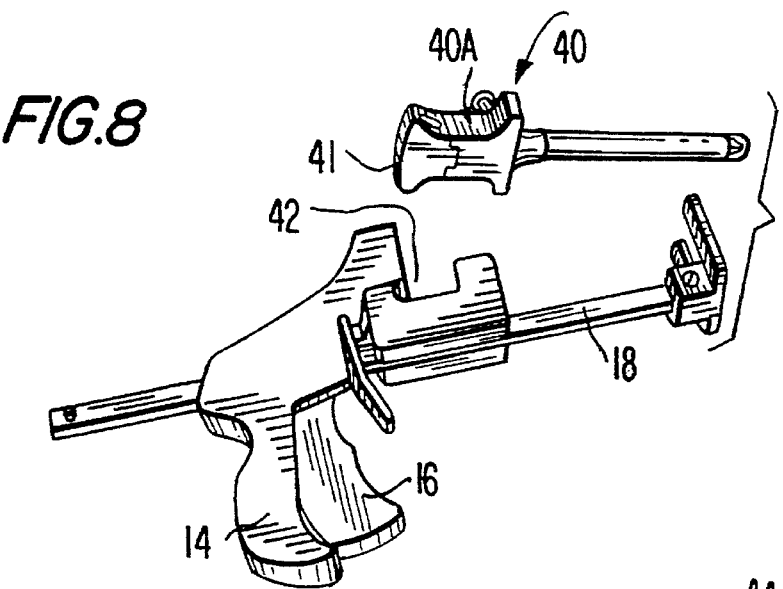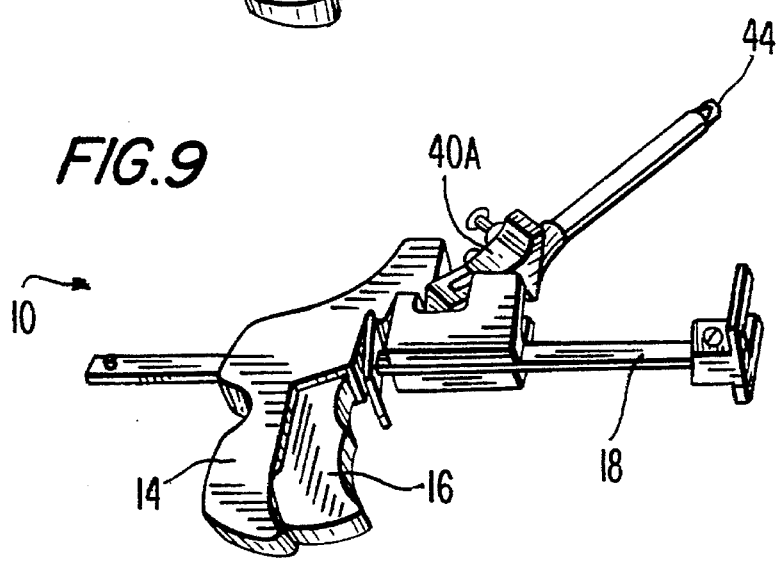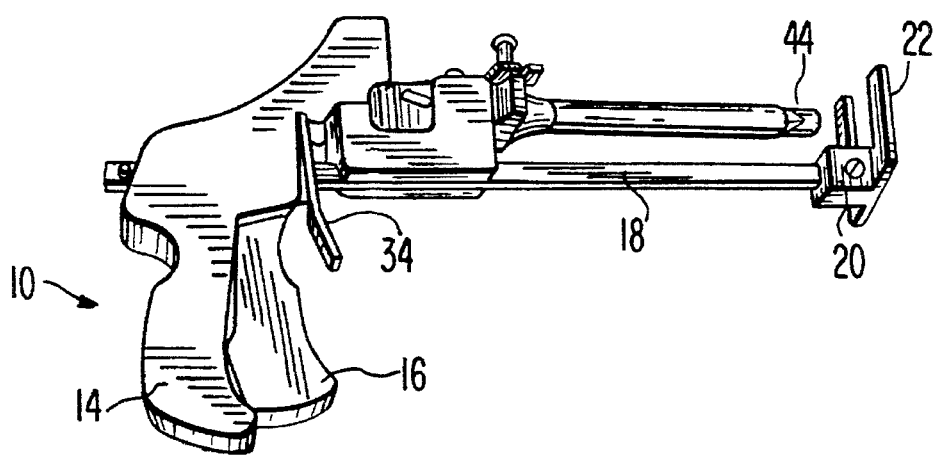

MECHANICAL TROCAR INSERTION APPARATUS

This is a continuation-in-part of co-pending U.S. application, Ser. No. 07/815,440 and of co-pending application, U.S. Ser. No. 07/815,488 both filed Dec. 31, 1991 and of co-pending application, U.S. Ser. No. 07/903,084, filed Jun. 17, 1992 the contents of which are incorporated herein by reference.

BACKGROUND OF THE INVENTION

This invention is in the field of trocars and apparatus for inserting trocars inwardly through an abdominal wall or other anatomical wall of a patient. Traditionally trocars have been inserted manually by a surgeon who holds the trocar in his hand or hands (a male is assumed merely for convenience of terminology herein) and directs the point of the obturator to a site on the surface of the abdomen which surface is prepared by forming a small straight line incision or X-shaped cut. The obturator is forcibly pushed in the axial direction through the skin and layers of muscle, fascia and peritoneum.

At the time of insertion the outer surface of the abdominal wall is either flat or somewhat convex as the patient lies on his back, and the trocar is inserted generally perpendicularly to that surface. For reasons as discussed below more fully, it is quite dangerous for the obturator to be inserted perpendicular to the surface without exercise of great control, because when the tip or point of the obturator penetrates this wall and enters the abdominal cavity it could easily nick, cut or otherwise damage an organ below.

One technique used by surgeons is to engage the abdominal wall with one hand, grasping a considerable portion of tissue and turning this mass of tissue somewhat transversely to adjacent portions of the abdominal wall, and then with the other hand aiming and inserting the trocar obturator through the wall in such a way that it travels in a direction generally parallel to the outer surface of the abdomen. This forcible penetration through a distorted tissue mass is awkward and greatly lacking in precise control over the process of insertion since the surgeon is pushing very hard against a resistance that cannot be precisely measured or predicted.

One device previously developed by the applicant herein for trocar insertion is an electrical power driven gun type apparatus which holds and forcibly directs a trocar by oscillating the trocar while directing it axially. In contrast to a surgeon manually pushing a trocar solely by the power in his hands, arms and upper body, this electrical power device provides a substantial amount of measured control during axial insertion, and also removes from the surgeon the necessity for using his own muscle power since the gun motor does most of the work. Also, by the gun's mechanism the axial motion is specific and controlled to be incremental, such that axial motion can be stopped very quickly at any time it is determined that the tip had penetrated the inner layer of the abdominal wall or the surgeon decides to stop for any reason. It is most difficult or impossible for a surgeon to stop forward motion in the midst of his own manual thrust with standard trocars.

The disadvantage of the above-described electro-mechanical apparatus is primarily its cost of manufacture. While the apparatus itself is very useful and operates as intended, the cost is a problem to hospital administrators who are concerned with economics of surgical procedures while seeking maximum use of new and better instruments.

Accordingly, the device of the present invention was developed to achieve insertion of a trocar with a minimum of physical effort by the surgeon since he will be using mechanical advantage achieved through the mechanism, and with a maximum control during the axial motion so that the above-described dangers are greatly minimized or reduced, while reducing cost of manufacture. Thus, it was desired that such new mechanism provide the advantages of the prior electro-mechanical device, but do so with a minimum of parts and cost of manufacture. This is especially true for hospitals which require these apparatus to be disposable. While it is obviously desirable for these and other surgical instruments to be autoclavable or otherwise sterilizable and reused, such is not always feasible or acceptable in this era of concern about AIDS and other transmittable diseases and infections. Accordingly, many people feel strongly that such instruments should be disposable. The present invention is a very simple, reliable, economical and totally mechanical device for holding and inserting a trocar, as disclosed and described herein.

SUMMARY OF THE NEW INVENTION

This invention is a gun type apparatus for holding and inserting a trocar/cannula assembly, particularly a disposable trocar/cannula assembly of common use. The new apparatus has a housing with means for receiving and holding the trocar and a handle with a pivotable trigger. The housing includes a guide to align the trocar and maintain alignment as the trocar is moved axially forward into and penetrating the patient's abdominal wall. The trigger is engaged to a mechanism whereby each successive pivoting movement of the trigger causes the trocar to move axially forward by a predetermined incremental distance.

In the preferred embodiment forward movement of the trocar is achieved as follows. An elongated spine or leg has a proximal or rear end and terminal or forward end terminating in a foot. The foot is placed against the patient's outer abdominal surface, and the spine is extended generally perpendicularly therefrom; this would be upward with a patient lying on his back. A body or housing of this new apparatus engages the spine and is adapted to slide axially in the forward direction. The housing has a handle and trigger. Each squeeze of the trigger drives the housing forward a predetermined incremental distance. The housing is adapted to receive and hold a trocar/cannula assembly which is carried by the housing and thus driven axially forward as the housing is propelled by trigger movement. The trigger mechanism is adjustable to control the drive increment.

The foot at the terminal end of the spine is adapted to engage an anchor pad of the type described in applicants' co-pending applications Ser. Nos. 07/815,488, 07/903,084 and 07/815,440, and as shown in FIGS. 1, 2, 3, 3A, 4, 5, 6, 7 and 7A in the drawings and described on pages 7–14 of the specification appended hereto as Appendix I from the parent application Ser. No. 07/903,084 of which the present application is a continuation-in-part. When the foot is appropriately engaged in an anchor pad the surgeon can pull the foot upward by pulling on the spine or on the housing engaged to the spine. For pulling on the housing the surgeon has one hand on the main handle below the housing and his other hand on a separate lifting lever or aid extending above the housing. The abdominal wall is somewhat elevated by prior insufflation, and the surgeon can supplement or render more secure this elevation by his manual pulling on the apparatus housing.

An ergonomic feature of this apparatus is the forward motion of the housing and handle as the trocar is held by the housing and driven axially forward. Thus, the housing and the surgeon's hand on the housing move axially toward the surface being penetrated, which for some surgeons is the natural sensation. Alternatively, the housing, handle and trigger may be in a fixed axial position on the spine, and each trigger pull can drive a plunger axially forward to push a trocar toward the forward end of the spine. Here, the result of axial insertion of the trocar is the same, but there is a psychological or physiological difference as regards how the surgeon's hand is pulling the trigger to cause trocar insertion while the housing and his hand remain axially stationary.

In the preferred embodiment disclosed herein the spine or leg, which may be rectangular or round in cross section, extends through an aperture in the trigger. As the trigger is squeezed and moved rearward, the housing and trocar are driven forward. Upon release of the trigger a spring pivots it forward to be ready for a successive squeezes and corresponding incremental forward moves of the trocar. This trigger movement may be set for maximum or it can be set and adjusted to any percentage of its full throw of pivoting movement for each squeeze thereof. Thus, the axial movement forward of the trocar can be accurately controlled in regard to the surgeon's hand movement.

The trocar optionally will have a sensing means to indicate at what point it has penetrated the inner layer of the abdominal wall at which time the surgeon will become aware and will cease any further forward drive motion of the apparatus.

Another feature of the device is a limit or set bar on the spine which can be preset before the insertion process begins. The presetting will be a determination by the surgeon of the total travel that he wishes to allow the trocar to make during the insertion. Then he squeezes the trigger repeatedly until the trocar has reached its limit and cannot move further forward or until the sensor has indicated that penetration is complete and he should stop.

After insertion is complete it is then necessary to remove the trocar from the insertion apparatus and withdraw the obturator from the cannula which remains inserted for the subsequent receipt of selected laparoscopic instrumentation. This apparatus provides a very simple and easy arrangement for separating the inserted trocar from the gun. The trocar is initially inserted into a portion of the housing of this gun by a simple pivoting motion into a small recess. After insertion of the trocar through the abdominal wall is complete, the trocar remains generally perpendicular to the surface having been penetrated, and the gun can be tipped and pivoted angularly with respect to the trocar, which is then easily slid off or released out of the recess in the gun's housing.

Normally the inserted trocar has an upper housing part which contains conventional valves for connection to suction or gas for pumping or insufflating the abdominal cavity and for inserting the laparoscopic equipment thereto. The preferred embodiment of this invention is shown in the drawings appended hereto and described as follows.

BRIEF DESCRIPTION OF THE DRAWINGS

FIG. 1A is an enlarged portion of FIG. 1;

FIG. 3 is a side elevation view similar to FIG. 1, but with a trocar cannula received and held in the housing of the insertion apparatus;

FIG. 4 is a top plan view of FIG. 3;

FIG. 8 is a bottom perspective view of the apparatus of FIG. 5 with a trocar poised for loading therein;

FIG. 9 is a view similar to FIG. 8 with a trocar in its initial position during loading;

FIG. 10 is a side elevation view of the apparatus showing the trocar in its fully loaded condition;

DETAILED DESCRIPTION OF A PREFERRED EMBODIMENT

Figure 1:
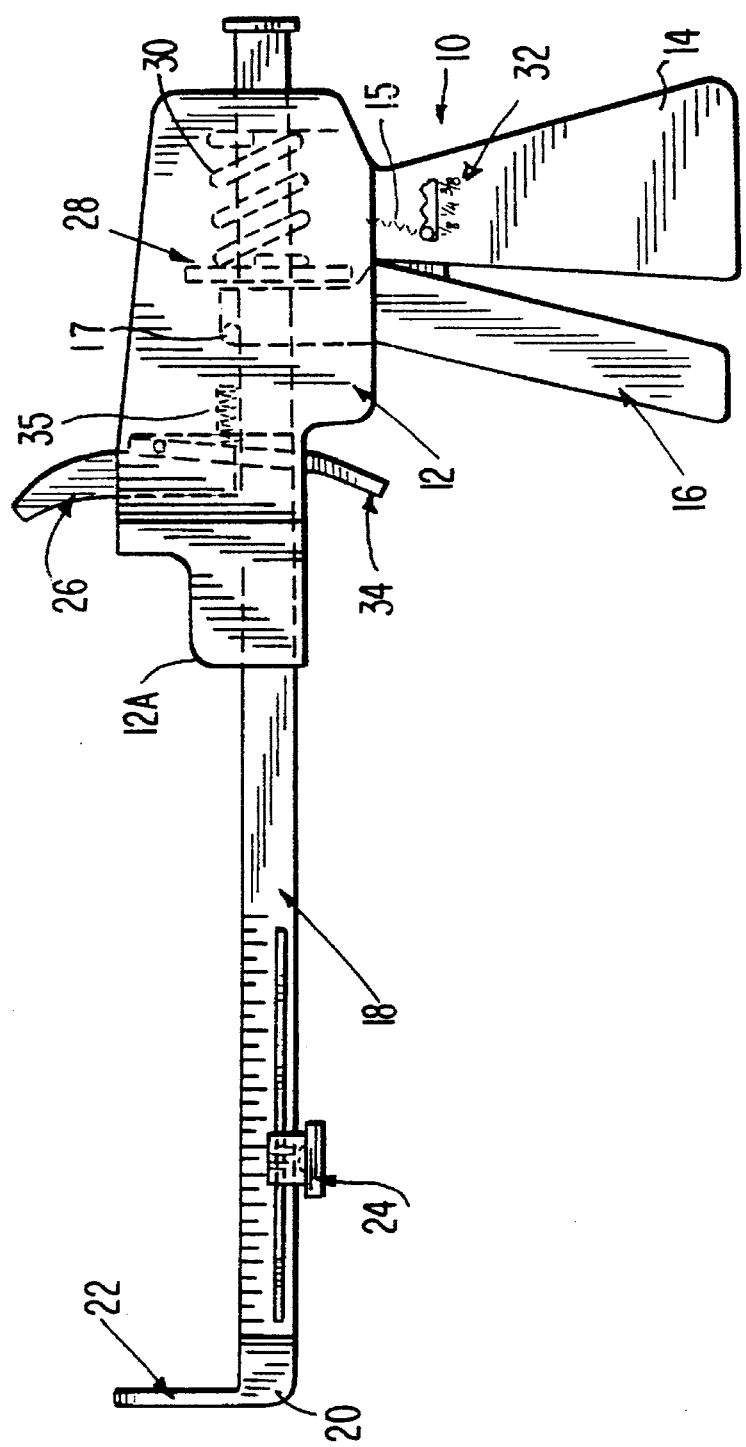
FIG. 1 is a schematic elevation view of the new trocar insertion apparatus.

In FIG. 1 the trocar insertion apparatus 10 includes a main body part 12 with a downward extending handle 14, adjacent pivotable trigger 16 and a forward extending spine 18. The terminal forward end of the spine turns upward and is divided to form a fork or foot 20 with two toes 22. On the spine between the foot at one end and the main body part at the other end is a depth stop element 24 for establishing the maximum depth that trocar may extend beyond the foot, as will be explained later. At the top of the main body part or housing 12 is a lift aid 26 which extends upward and can be easily engaged by the surgeon's second hand while his first hand holds the handle and trigger.

Inside the housing 12 are 3 mechanisms for the mechanical operation hereof. The principle mechanism is associated with trigger 16 which pivots about pivot point 17. Adjacent and immediately rearward of the trigger is an element designated forward catch 28, and adjacent and rearward of that is a spring 30 formed as a coil spring situated to exert a forward force against the forward catch and to force the catch forward to a new starting position after each trigger pull. Accordingly, when the trigger 16 is squeezed and pulled rearward it has to overcome the forward thrust of spring 30 acting against forward catch 28 acting against the trigger.

Figure 23:
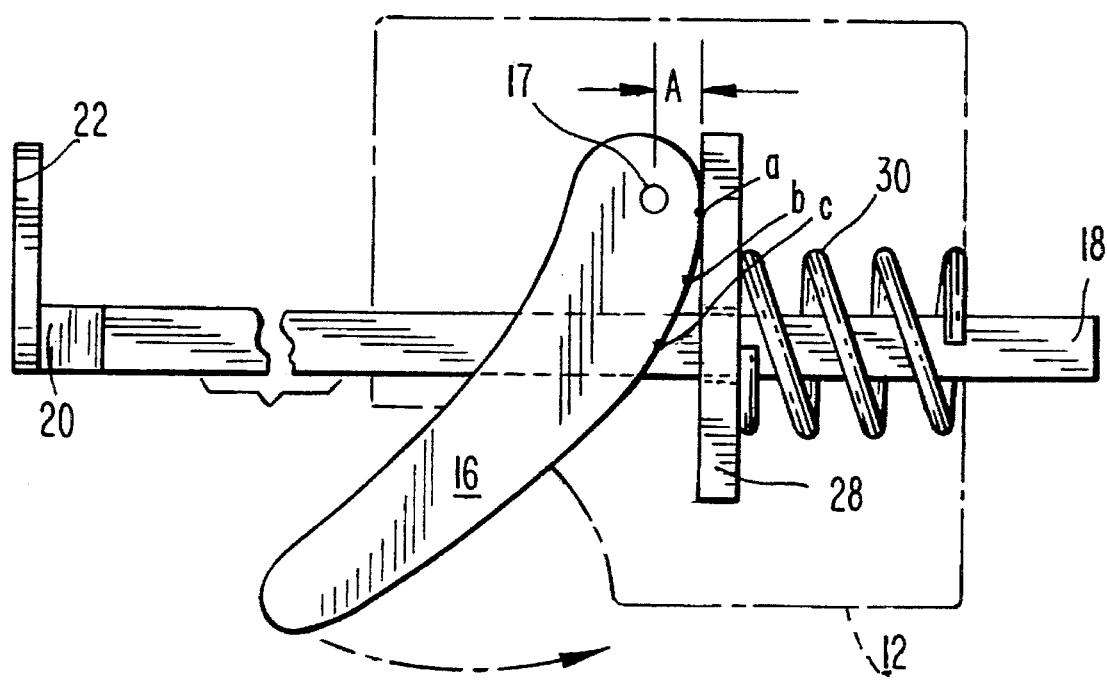
FIG. 23 is a fragmentary schematic view of the trigger and drive mechanism in FIG. 1, showing the trigger in extended, cocked position.
Figure 24:
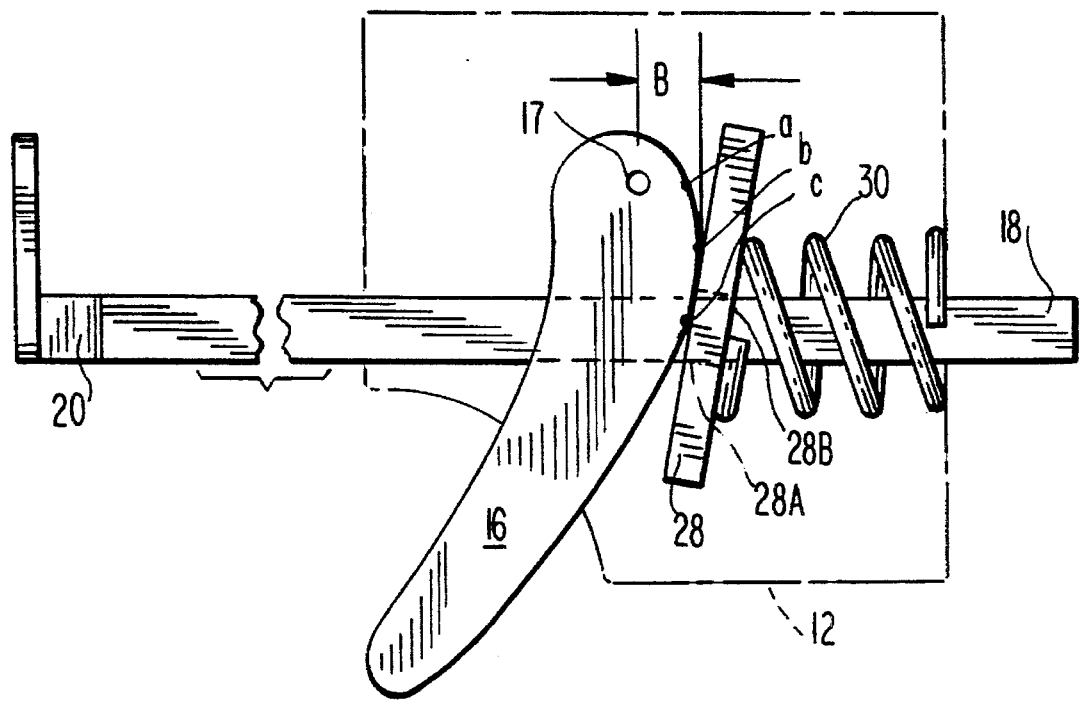
FIG. 24 is similar to FIG. 23 with the trigger shown in a partially squeezed condition and the housing moved partially forward on the spine.
Figure 25:
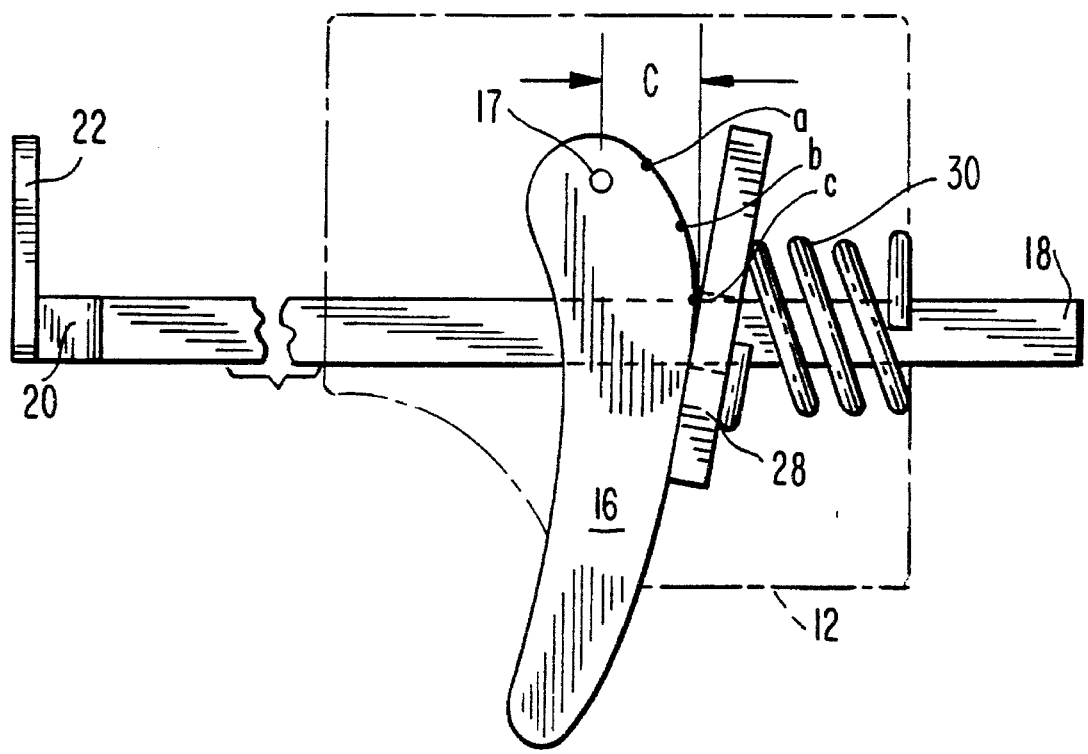
FIG. 25 is similar to FIG. 24 with the trigger shown in a fully squeezed condition and the housing moved further forward on the spine.

As seen in FIGS. 23–25 the trigger 16 has a cam surface indicated by points a, b and c, each being successively farther away from pivot point 17. As seen in FIG. 23 point a is distance A from pivot point 17; point b is at distance B; and point c is at distance C, whereby A, B and C represent the effective lengths of the cam as the trigger is pivoted from its initial or start position to its pulled or final position.

The spine in this embodiment has rectangular cross section. The forward catch 28 is a generally rectangular shape plate with a rectangular aperture therethrough which receives the rectangular spine extending through said aperture. The height of the aperture is slightly greater than height of the spine. Since the aperture in the forward catch has slightly greater dimensions than the spine, the spine could slide freely through the said aperture. As seen in FIGS. 1, 2, and 23–25, when the trigger is pulled and it presses against this forward catch or plate 28, said plate is caused to tilt slightly and the bottom edge 28A of its aperture digs into and engages the adjacent bottom surface of the spine. Also the top edge 28B of the aperture digs into and engages the adjacent top edge of the spine. The catch becomes locked against the spine. Further pivoting of the trigger against the catch as seen in FIG. 24 causes a cam surface b of the trigger to bear against the catch plate. Surface b is at a greater distance than surface a from the pivot point 17; this causes the pivot point, axle therethrough and housing that supports the axle, all to be driven forward a distance indicated as B.

The housing 12 is represented schematically by the dotted outline in FIGS. 23–25. It can be seen that as the trigger is pivoted a first amount from FIGS. 23 to 24 and a second amount from FIGS. 24 to 25, that the cam surface on top of the trigger drives the housing forward corresponding amounts B and C. Upon release of the trigger the spring pushes the trigger to pivot forward and the spring also presses against the catch plate and returns it to its position shown in FIG. 1. Each squeezing of the trigger causes a successive tilting of the forward catch plate and a corresponding slight movement forward of the housing. Each return of the trigger 16 allows the catch plate 27 as driven by spring 30 to move toward the left from distance C of FIG. 25 to distance A of FIG. 23, where the catch plate establishes a new starting point on the spine against which the trigger's cam pushes the housing forward with a trigger pull. The trigger can be successively or consecutively pulled until the housing is driven forward its full travel or until the depth stop element 24 bars further movement of the trocar or housing. The general principal of a one way drive means on a bar including brake means to prevent reverse motion unless released is know, as exemplified in U.S. Pat. Nos. 5,005,449 and 4,926,722.

Associated with trigger 16 is a regulation mechanism 32 seen in FIG. 1 which can be arranged to limit the rearward pivoting motion of the trigger to a preset amount. Element 32A is a strip that slides horizontally in handle 14. At the right end of this strip is a pin 15a that may engage any of three grooves 14a, depending on the position of the strip. Spring 15 urges the pin to securely engage one groove. The forward end 33 of strip 32A serves as a stop to determine how far the trigger can pivot. Thus, the position of strip 32A is adjustable to control maximum trigger pull and maximum trocar movement. Below the grooves 14a are indicia to indicate the setting. Typical settings might be ⅛", ¼" and ⅜". Accordingly each time the trigger is pulled it can move only the predetermined maximum distance. This prevents the surgeon from inserting the trocar at too rapid a rate. Stated otherwise, the limiting of the trigger motion can directly determine the amount of forward motion the trocar with each squeeze of the trigger.

Another mechanism within the housing as seen in FIG. 1 is reset lever 34 which is intended to allow the housing to be moved rearward and returned to its original position after it has been driven forward by a succession of trigger pulls. This reset lever, also called reversing catch, is designed to engage the spine and prevent the housing from moving rearward unless and until this reset lever is released. It operates somewhat similarly to the catch plate 28 in that it has an aperture of dimensions generally corresponding to those of the spine which allows the spine to pass through it under normal conditions. However, the spring 35 presses against this lever putting it in a tilted position whereby one of its edges of its aperture engages against the adjacent surface of the spine, thereby locking it in position from moving axially until such lever is pulled to release the housing to go rearward.

In FIG. 1 the lift aid 26 is basically a fixed handle whereby the surgeon can stabilize or guide the apparatus with one hand while his other hand holds handle 14. FIGS. 3 and 4 show the apparatus of FIG. 1 with the trocar cannula loaded onto the device. The trocar 40 is a disposable type and is known engaged in the upper portion of the housing immediately above the spine.

Figure 5:
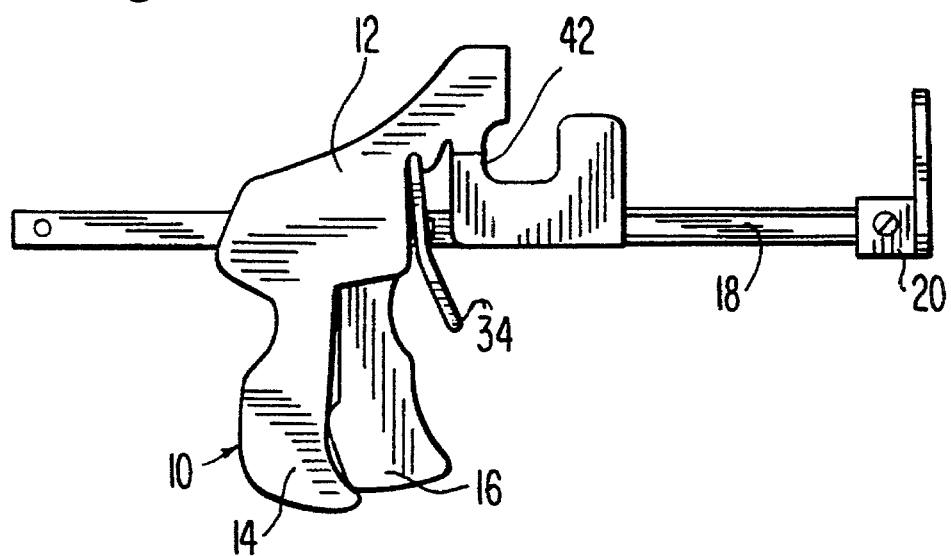
FIG. 5 is a side elevation view of a preferred embodiment of the insertion apparatus represented by FIGS. 1 and 2 before a trocar cannula has been loaded therein.
Figure 6:
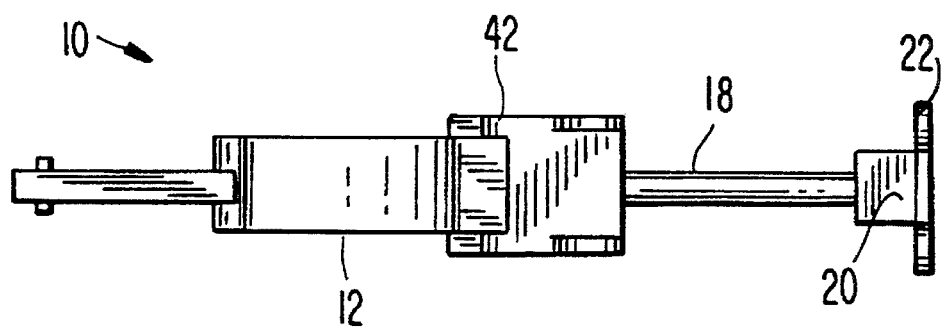
FIG. 6 is a top plan view of FIG. 5.
Figure 7:
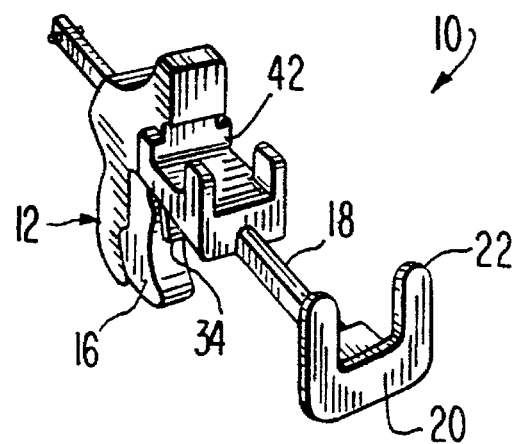
FIG. 7 is a front perspective view of FIG. 5.

FIGS. 5–7 shows this apparatus with the same basic elements as have been described with regards to the schematic views of FIGS. 1 through 4. For convenience, the same reference numerals will be used for the basic elements, and then additional reference numerals will be used as regards elements or features which are slightly different or in addition to those shown in the earlier figures. Accordingly, housing 12 in FIG. 5 has a recess 42 for receiving the rear end of the trocar housing.

Figure 11:
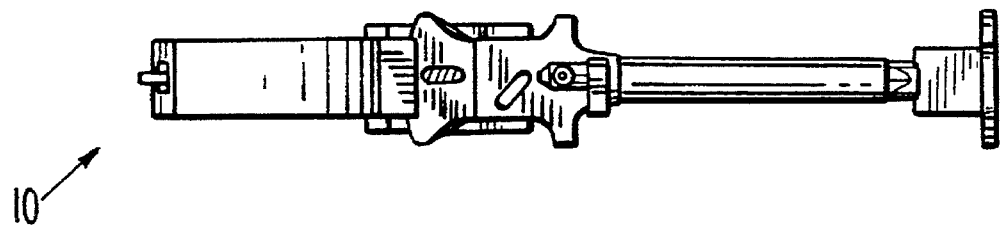
FIG. 11 is a top plan view of the apparatus of FIG. 10 with the trocar in the fully loaded condition.
Figure 12:
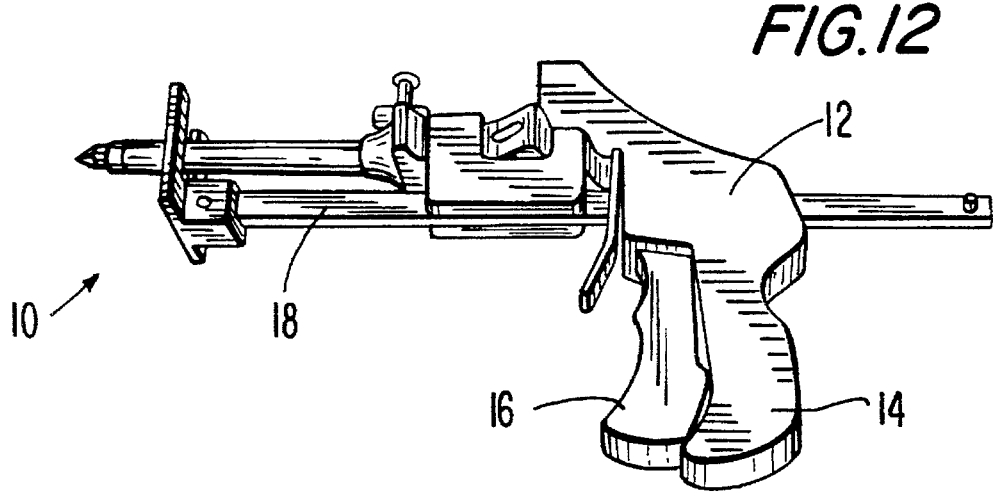
FIG. 12 is a side elevation view of the apparatus with the trocar loaded and driven forward about 50% of its full travel.
Figure 13:
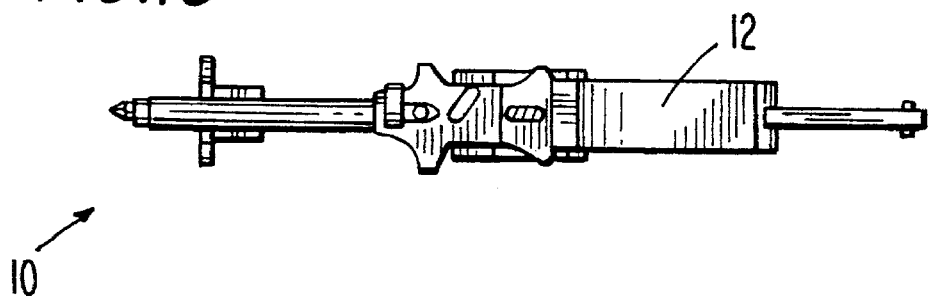
FIG. 13 is a top plan view of FIG. 12.
Figure 14:
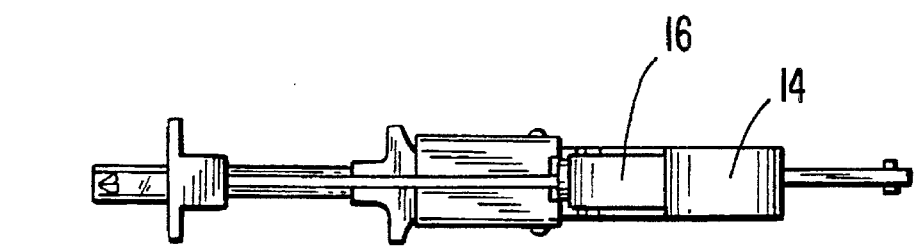
FIG. 14 is a bottom plan view of FIG. 12.
Figure 15:
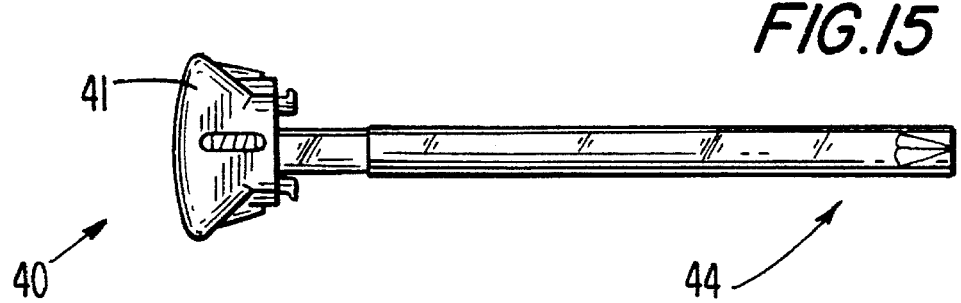
FIG. 15 is a top plan view of a trocar obturator.
Figure 16:
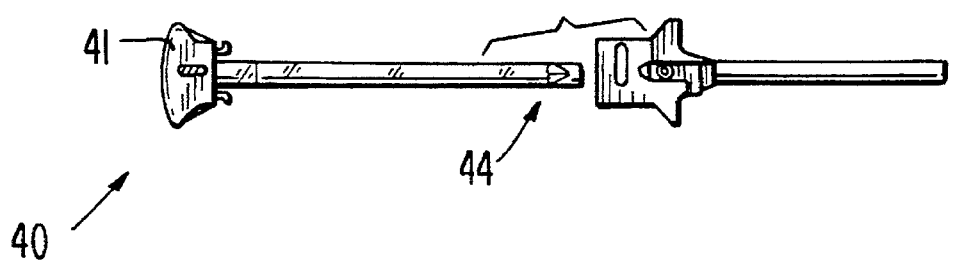
FIG. 16 is a top plan view of this trocar obturator of FIG. 15 positioned for insertion into the trocar housing and cannula.
Figure 17:
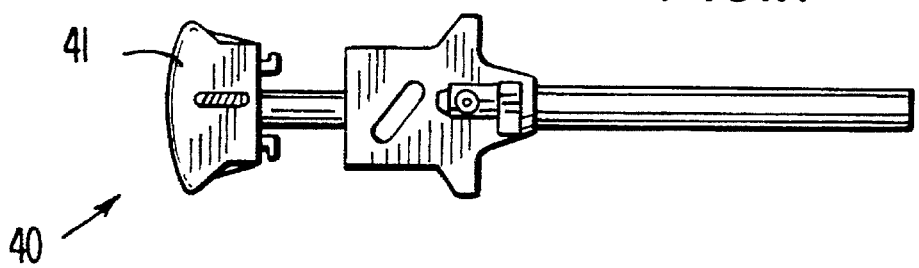
FIG. 17 is a top plan view of the trocar obturator partially inserted into the trocar housing and cannula.
Figure 18:
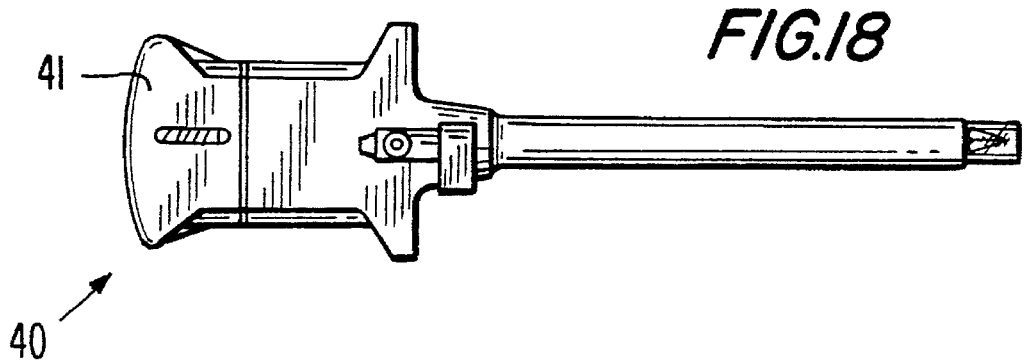
FIG. 18 is a top plan view of the trocar obturator fully inserted into the trocar housing.

FIGS. 8–11 shows the apparatus of FIG. 5 with the trocar 40 and its housing 40A positioned above and near recess 42 into which it will be inserted. FIG. 9 shows the top end 41 of the trocar housing tilted at about 45 degrees and in its initial insertion position in said recess. FIG. 10 shows the trocar cannula tilted downward into a position parallel to spine 18 with the trocar housing fully inserted and seated in the recess 42 and the tip of the obturator 44 positioned rearward of the foot 20 and the fork or toes 22 at the front terminal end of this apparatus. The shape and dimensions of the upper trocar housing 41 have been considered in the design of the recess 42 such that this trocar housing can easily be inserted into the recess, but the recess will engage and capture the trocar housing and hold it securely during the insertion process. FIG. 11 shows the apparatus of FIG. 10 with the trocar cannula loaded and ready for insertion. FIGS. 12, 13 and 14 show side, top and bottom views of this apparatus with the trocar driven about 50 percent of its length forward along the spine.

After a trocar cannula is fully inserted, the insertion apparatus can be readily separated from the cannula by holding the cannula and angling the apparatus with respect to the cannula, generally opposite to the cannula loading procedure.

There are a number of alternative mechanisms possible for causing the housing and the trocar to move relative to the spine and foot. Instead of a pivoting trigger with its catch mechanism biting into the spine with each squeeze, it would be possible for example to use a rack and pinion gear operation, or still other forms of wheel drive mechanisms using gears or friction.

The housing and its recess for receiving a trocar can be adapted to receive all commercial styles of disposable trocars. The recess can be shaped to accommodate different trocar housings, or adaptors can be provided to be inserted into or onto the housing to accommodate different trocar housings if they differ substantially from the one made especially for this apparatus. This recess is intended to be extremely simple for receiving the disposable trocar quickly and easily and require no secondary locking mechanism. Its engagement and secure locking is automatic merely by angling and positioning it in a recess where it remains securely locked until the surgeon positively releases it as may be required. Also it is possible to add a secondary or auxiliary locking mechanism for additional security.

It is intended that the disclosure above and objectives and preferred embodiment are merely illustrative and not limiting of the invention which is defined by the claims appended hereto. Within the scope and spirit of these claims many variations in structure and mechanism are possible.

APPENDIX I anatomical wall or relative to the stabilizer base. As disclosed herein, there are numerous embodiments for engaging the trocar and restricting it from tipping and/or axial movement.

BRIEF DESCRIPTION OF THE DRAWINGS

Figure 2:
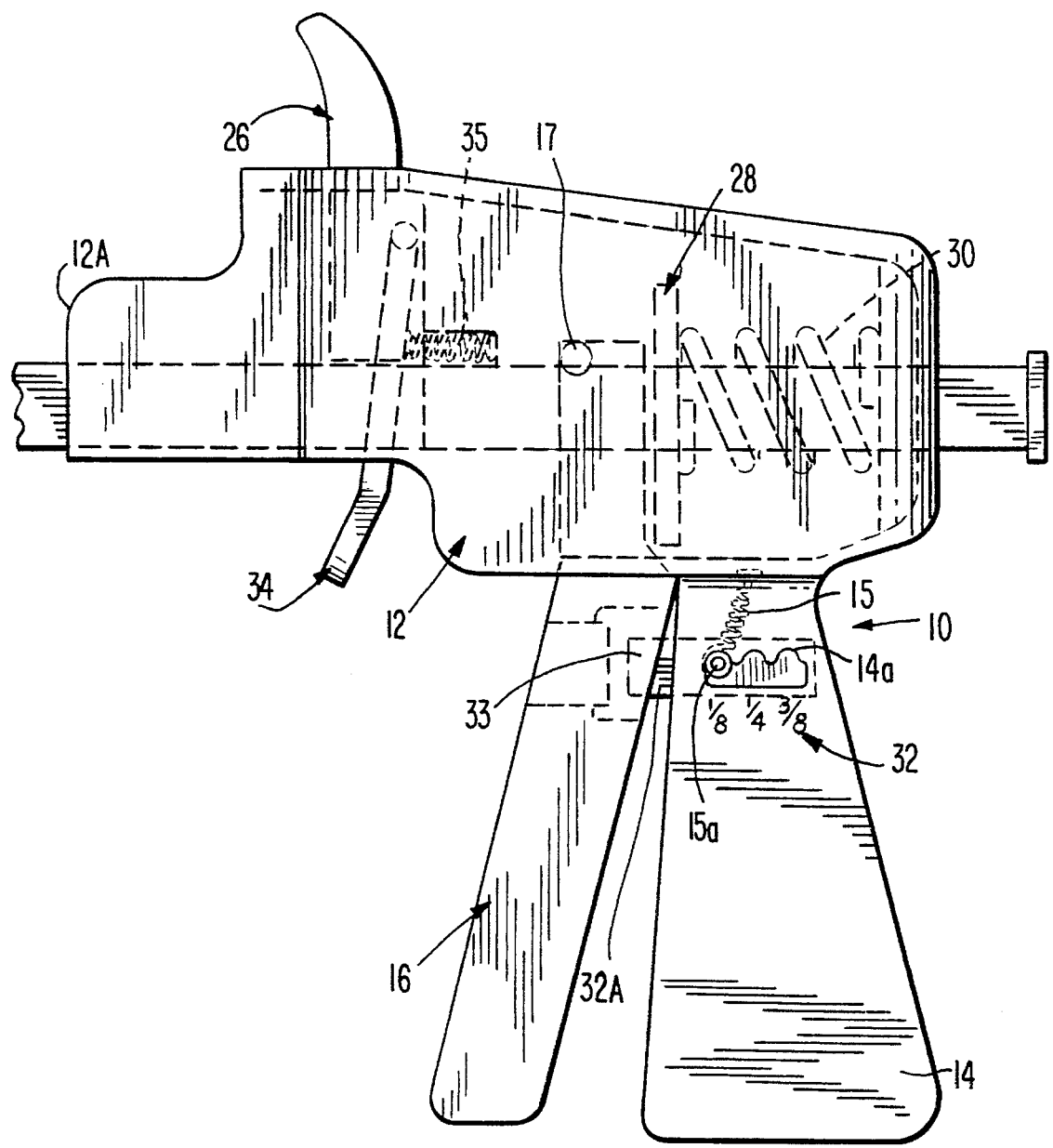
FIG. 2 is a top plan view of FIG. 1.
Figure 19:
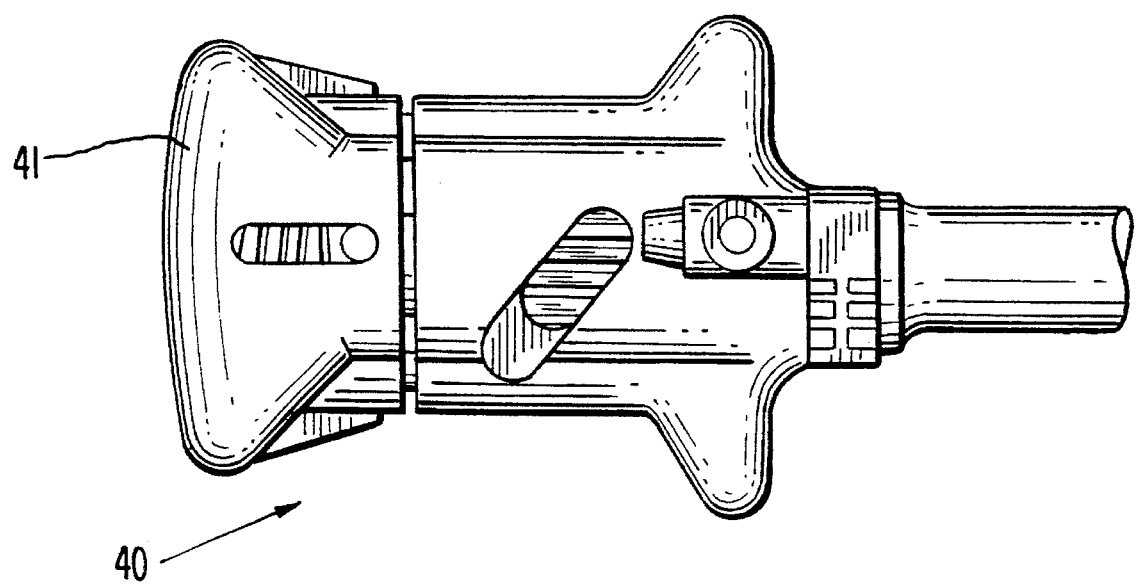
FIG. 19 is an enlarged fragmentary view of the trocar housing with the obturator fully inserted.
Figure 20:
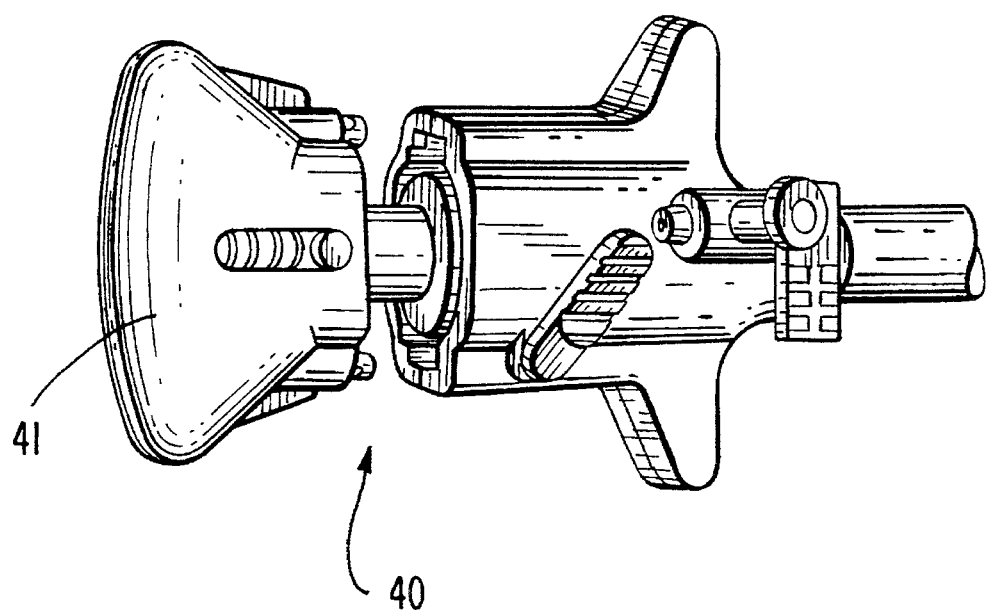
FIG. 20 is a similar view to FIG. 19 with the trocar obturator partially withdrawn from the housing.
Figure 21:
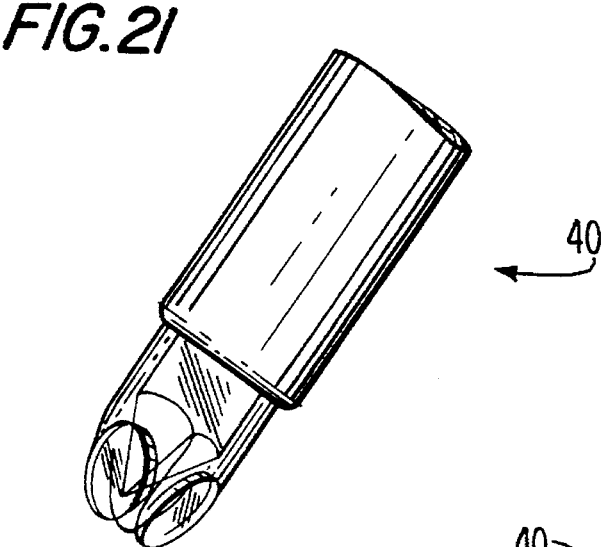
FIG. 21 is an enlarged front perspective view of the tip of the trocar obturator with a safety shield extended beyond the metal tip.
Figure 22:
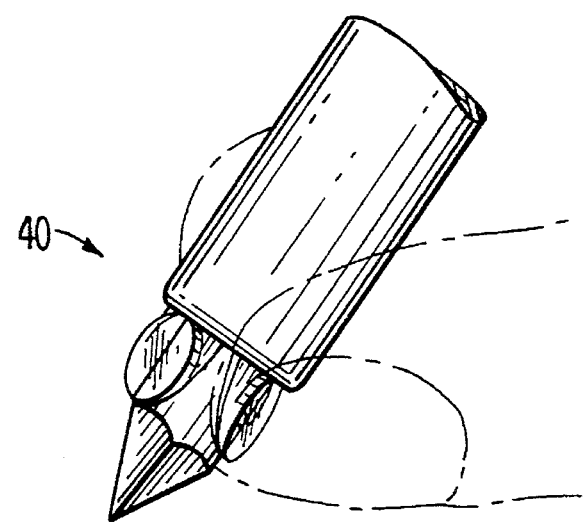
FIG. 22 is an enlarged fragmentary view of a trocar obturator with the tip extended beyond the safety shield or alternatively with the safety shield retracted actually to expose the tip of the obturator.

Fig. 1 is a front perspective view of a new trocar insertion apparatus as used with a first embodiment of the anchor pad of the new invention;

Fig. 2 is a top perspective view of the anchor pad of Fig. 1;

Fig. 3 is a fragmentary cross-section showing schematically a trocar applying downward force and inward displacement and distension of the abdominal wall;

Fig. 3A is a fragmentary cross-section showing the new anchor pad applying counteracting upward force;

Fig. 4 is a schematic side elevation view of a second embodiment of an anchor pad;

Fig. 5 is a schematic side elevation view of a third embodiment of an anchor pad with an upper stem releasably coupled to a trocar insertion apparatus;

Fig. 6 is a fragmentary front perspective view of the anchor pad of Fig. 5;

Fig. 7 is a top perspective view of a fourth embodiment of an anchor pad having a button-type engagement means;

Fig. 7A is a side elevation view of the anchor pad of Fig. 7;

Figs. 7B and 7C are side elevation views of two further embodiments of Fig. 7A;

Fig. 19 is a perspective view of a third embodiment of a stabilizer anchor pad;

Fig. 20 is a perspective view of a fourth embodiment of a stabilizer anchor pad;

Fig. 21 is a perspective view of a fifth embodiment of a stabilizer anchor pad;

Fig. 22 is a perspective view of a sixth embodiment of a stabilizer anchor pad;

Figs. 22A - 22C show a variation of the device of Fig. 22.

Fig. 23 is a perspective view of a seventh embodiment of a stabilizer anchor pad;

Fig. 24 is a top plan view of Fig. 23;

Fig. 25 is a sectional view taken along lines I-I of 23.

Fig. 26 is a perspective view of an eighth embodiment of a stabilizer anchor pad in its initial flat state;

Fig. 27 is a perspective view of the stabilizer anchor pad of Fig. 26 in its trocar-engaging state;

Fig. 28 is a perspective view of a ninth embodiment of a stabilizer anchor pad in its initial flat sate;

Fig. 29 is a perspective view of a stabilizer anchor pad of Fig. 28 in its trocar-engaging state;

Fig. 29A shows a variation of the device of Fig. 29;

Fig. 30 is a perspective view of a tenth embodiment of a stabilizer anchor pad, shown in separated parts;

Fig. 31 is a perspective view of the stabilizer anchor pad of

Fig. 30, shown in assembled state;

Fig. 32 is a perspective view of the stabilizer anchor pad of Fig. 31 with alternative latch means;

Fig. 32A is a perspective view of another embodiment of the hinged collar stabilizer of the type shown in Fig. 32;

Fig. 32B is a perspective view of an alternative latching means for the anchor pad of Fig. 31;

Fig. 33 is a perspective view of a twelfth embodiment of a stabilizer anchor pad including means for pulling;

Fig. 34 is a perspective view of a thirteenth embodiment of a stabilizer anchor pad including means for pulling;

Figs. 35A-35C are perspective, top plan and sectional views respectively showing another embodiment of a trocar stabilizer;

Figs. 35D, 35E and 36 are sectional views of three variations of the device shown in Figs. 35A-35C;

Figs. 37A and 37B are perspective and sectional views respectively of an insertion and stabilizer pad for a Veress needle;

Figs. 38 and 39 are sectional views of further stabilizing anchor pad embodiments for use with needles and trocars; and Figs. 40 and 41 are sectional views of further variations of releasable anchor pads for use with trocar insertion apparatus.

DETAILED DESCRIPTION OF THE PREFERRED EMBODIMENTS

General Features

The new anchor pad is usable with new power-drive trocar insertion apparatus as shown schematically in Figs. 1, 4 and 5 herein and with older style manually driven apparatus as schematically shown in Fig. 10 herein. In all embodiments the new anchor pad has means on its lower side for engaging the top surface of skin generally adjacent the point of insertion and further means on the pad to be engaged and urged upward for countering the downward force of a trocar when it is inserted. The upward force may be applied either: (a) by an upward pull on the pad as may be applied by the surgeon or his aide or by other external means and thus an upward pull on the skin generally adjacent the area of insertion, or (b) by the effective upward force as may be applied by the insertion device itself as its feet or other part engage the pad and resist the downward force applied by the trocar. The downward force is transferred by the trocar to the skin in and adjacent the insertion area and thence to the adhesive and the anchor pad in contact with that skin. The trocar insertion apparatus is held by the surgeon or by other means so that its feet engaged to the adhesed anchor pad resist the displacement by the downward force applied to the pad via the downward drive of the trocar and cannula.

The new anchor device or anchor pad is formed of a layer of rubber, plastic, cloth or other material suitable for use in an operating room and for contract with a patient's skin. The pad could vary in dimensions, with five or six inches square being the size of one embodiment. On the bottom surface of the pad is a layer of adhesive suitable for operating room use and non-toxic to a patient's skin. Also this adhesive should be very strong with respect to perpendicular separation of the pad from the skin. Lastly, this adhesive should be readily releasable or removable when the procedure is complete. This releasability might be accomplished by selecting an adhesive that dissolves in alcohol or other common solvent in the operating room, or by selecting an adhesive that is strong regarding normal perpendicular forces, but peels off easily. The adhesive could be a layer applied to the pad at the time of its manufacture or an adhesive applied at the time of surgery.

Detailed Features

Fig. 1 shows a front perspective view of a new anchor pad 1 of this invention as used with a power-drive trocar insertion apparatus 10 having a trocar housing 12, a cannula housing 14, a handle 16, a frame 18 and feet 20 at the bottom of the frame. The trocar and cannula 22, 24 extend downward through the feet. The anchor pad 1 as seen in Figs. 1 and 2 comprising the body part 28, adhesive 30 on the bottom of the body part, loops or stirrups 32 on top of the pad for engaging and applying the counter-traction upward force to the pad, and aperture 34 for passage of the trocar and cannula. This aperture is optional depending on the overall shape of the pad.

As seen in Fig. 3 the trocar 22 receives axial force indicated by arrow 36 leading to penetration indicated by arrows 38. The inner surface of the peritoneum or body cavity is shown in solid line 40 prior to penetration and in dotted lines 42 as it is penetrated by a conventional trocar without benefit of the new anchor pad. Thus, line 42 shows the distended shape of the peritoneum due to the trocar's force, with bracket 42A indicating the invagination of the abdominal wall. In Fig. 3A arrows 46 indicate the counteracting upward force applied by the pad to the top surface of the skin when engaging means 32 is pulled upward. The result of this secure and non-traumatic counter-traction will be greatly lessened distention of the lower surface 40 of the peritoneum than usual without the anchor pad.

Fig. 4 shows a further variation of the anchor pad with clips or hooks 48 for engaging feet 50 of the frame or base of a power trocar insertion apparatus 52.

Figs. 5 and 6 show an anchor pad 54 with upward stem 56 that is adapted to receive a downward stem 58 of a trocar insertion apparatus. At the top of stem 56 is a coupling and release means 60 to allow separation of the two stems by axial upward motion of the apparatus 52 without any lateral motion which might disturb the cannula positioning.

Fig. 7 shows another embodiment 68 of the anchor pad with an alternate means 70 in the form of a button for engaging the foot 72 or feet of a power insertion apparatus. Fig. 7A shows the button 70 in side elevation view along with pad 68 and adhesive 74. Figs. 7B and 7C show variations of the anchor pad of Fig. 7 which are discussed later.

Fig. 8 shows an anchor pad 75 similar to that of Fig. 2, but without an aperture.

Fig. 9 shows another pad 76 with upper engaging means 78 and peel-up adhesive strips 80 which can subsequently be used as shown in Fig. 9A to engage and securely hold the inserted cannula 82. The tape or other engaging means helps to secure the cannula from any inadvertent axial or lateral movement and slippage and thus helps to stabilize the associated laparoscopic apparatus.

Fig. 10 shows schematically a conventional trocar, cannula device 84 with palm and finger grips 86, 88, which device is inserted by manual axial force applied by the surgeon. The new anchor pad is useful with such conventional trocar insertion devices as well as with power insertion devices as described above. For the conventional device the anchor pad does not necessarily become engaged to any part of the insertion device, but is used in conjunction and simultaneously with the anchor pad, whereby the pad is adhered to the skin closely adjacent the insertion area and pulling means on the pad are pulled outward providing secure non-traumatic counter-traction while the trocar is pushed inward. One representative anchor pad 90 is shown in Fig. 11 with pulling means 92 in the form of straps with finger loops to be pulled by the surgeon himself or by an aid or by other means. These loops enable the surgeon alone to control both sides of the insertion site, without requiring the use of an assistant.

We claim:

1. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said drive means adapted to provide a small controlled incremental axial movement of said housing each time it is actuated, said apparatus further comprising actuator means for actuating said drive means to provide said movements whereby the trocar/cannula carried by said housing is movable axially along said spine, said apparatus further comprising (a) an anchor pad which has a base securable to the outer surface of said anatomical wall and a body part adapted to be engaged and pulled generally perpendicularly with respect to said base, and (b) engaging means extending from said spine for engaging said body part of said anchor pad, whereby said apparatus when its engaging means is engaged to an anchor pad and pulled in its proximal direction may pull said anatomical wall outward while a trocar/cannula assembly is being inserted by said apparatus through said wall in the terminal direction of the spine.

2. An apparatus according to claim 1 wherein said housing has a handle part engageable by a surgeon's hand, said actuator means comprising a moveable trigger adjacent said handle and movable by the surgeon's finger.

3. An apparatus according to claim 2 wherein each trigger movement provides an axial movement of the housing of predetermined distance, and said trigger may be pulled successively to drive the housing and trocar axially along said spine.

4. An apparatus according to claim 2 further comprising trigger adjustment means for varying the maximum trigger movement with each trigger pull and thereby varying the corresponding maximum axial movement of the housing with each trigger pull.

5. An apparatus according to claim 2 wherein said trigger is pivotably mounted on said housing and movable between its forward and rearward positions corresponding to the terminal and proximal direction respectively, said drive means further comprises a spring urging said trigger toward its forward position, said spine having a catch-plate thereon, said trigger further comprises a cam surface which becomes effectively longer as the trigger is pivoted toward its rearward position, said cam surface situated to bear against said catch plate on the spine, whereby pivoting of the trigger pivotally coupled to the housing causes the housing to be driven axially on said spine a distance corresponding to the effective length of the cam.

6. An apparatus according to claim 5 wherein said catch plate moves axially forward to a new start position on said spine each time said trigger returns from its rearward to its forward position, thereby providing start positions of the housing successively axially forward with each pull and return of the trigger.

7. An apparatus according to claim 6 wherein said catch plate has an aperture through which said spine extends, said spring that urges said trigger forward simultaneously urges said catch plate forward, said aperture corresponding closely in size to the cross-section of the spine, whereby the spring force against the catch plated moves it easily axially on the spine, but force from the trigger's cam tilts the catch plate causing edges of its aperture to tightly engage and axially lock against said spine.

8. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position, said apparatus further comprising (a) an anchor pad which has a base securable to the outer surface of said anatomical wall and a body part adapted to be engaged and pulled generally perpendicularly with respect to said base, and (b) engaging means for engaging said body part of said anchor pad, whereby said apparatus when its engaging means is engaged to an anchor pad and pulled in its proximal direction may pull said anatomical wall outward while a trocar/cannula assembly is being inserted by said apparatus through said wall in the terminal direction of the spine.

9. An apparatus according to claim 8 wherein said trocar/cannula assembly has a housing part at its proximal end and an obturator stylet at its terminal end, said holding means includes a recess for receiving said housing part of the trocar/cannula assembly and for holding firmly said housing part while said trocar/cannula assembly is directed axially toward said terminal end of the spine.

10. An apparatus according to claim 8 wherein said engaging means is situated at said terminal end of said spine.

11. An apparatus according to claim 8 wherein said engaging means comprises a foot at the spine's terminal end which extends transversely of the spine's axis.

12. An apparatus according to claim 11 wherein said foot comprises a pair of spaced apart toes for engaging said body part of the anchor pad.

13. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said apparatus further comprising (a) an anchor pad which has a base securable to the outer surface of said anatomical wall and a body part adapted to be engaged and pulled generally perpendicularly with respect to said base, (b) engaging means extending from said spine for engaging said body part of said anchor pad, and (c) lift means adapted to be engaged and pulled axially in the direction of the proximal end, said lift means when pulled applying an axial force to said engaging means and thence to said anchor pad, whereby said apparatus when its engaging means is engaged to an anchor pad and pulled in its proximal direction may pull said anatomical wall outward while a trocar/cannula assembly is being inserted by said apparatus through said wall in the terminal direction of the spine.

14. An apparatus according to claim 13 wherein lift means extends from said housing as a handle engageable by a surgeon's hand.

15. An apparatus according to claim 14 wherein said engaging means extends from the terminal end of said spine, whereby pulling on said lift means applies a force via said housing through said spine coupled to the housing to said engaging means and thereby to the anchor pad.

16. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said apparatus further comprising (a) an anchor pad which has a base securable to the outer surface of said anatomical wall and a body part adapted to be engaged and pulled generally perpendicularly with respect to said base, (b) engaging means extending from said spine for engaging said body part of said anchor pad, and (c) means for re-setting said apparatus after the housing has been driven to its final position, by facilitating rearward movement of the housing toward the proximal end of the spine to its initial position where the housing can receive a trocar/cannula, whereby said apparatus when its engaging means is engaged to an anchor pad and pulled in its proximal direction may pull said anatomical wall outward while a trocar/cannula assembly is being inserted by said apparatus through said wall in the terminal direction of the spine.

17. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said 18. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said apparatus further comprising (a) an anchor pad which has a base securable to the outer surface of said anatomical wall and a body part adapted to be engaged and pulled generally perpendicularly with respect to said base, and (b) engaging means extending from said spine for engaging said body part of said anchor pad, whereby said apparatus when its engaging means is engaged to an anchor pad and pulled in its proximal direction may pull said anatomical wall outward while a trocar/cannula assembly is being inserted by said apparatus through said wall in the terminal direction of the spine, and wherein said trocar/cannula has a housing part at its proximal end and an obturator at its terminal end, said holding means includes a recess for receiving said housing part of the trocar/cannula and for holding firmly said housing part while said obturator is directed axially toward said terminal end of the spine and while said housing and trocar/cannula are moved along the spine in its terminal end direction, and wherein said recess is adapted to receive said trocar/cannula housing when said trocar is initially angularly directed into the recess and subsequently aligned axially with said spine, and said recess is further adapted to release said trocar by inclining said recess angularly with respect to said inserted trocar, whereby the apparatus is then separated from the trocar/cannula.

19. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said apparatus further comprising (a) an anchor pad which has a base securable to the outer surface of said anatomical wall and a body part adapted to be engaged and pulled generally perpendicularly with respect to said base, (b) engaging means extending from said spine for engaging said body part of said anchor pad, and auxiliary holding means for further releasably securing the trocar/cannula in said holding means whereby said apparatus when its engaging means is engaged to an anchor pad and pulled in its proximal direction may pull said anatomical wall outward while a trocar/cannula assembly is being inserted by said apparatus through said wall in the terminal direction of the spine, and wherein said trocar/cannula has a housing part at its proximal end and an obturator at its terminal end, said holding means includes a recess for receiving said housing part of the trocar/cannula and for holding firmly said housing part while said obturator is directed axially toward said terminal end of the spine and while said housing and trocar/cannula are moved along the spine in its terminal end direction, and auxiliary holding means for further releasably securing the trocar/cannula in said holding means.

20. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said apparatus further comprising an anchor pad which has a base securable to the outer surface of said anatomical wall and a body part adapted to be engaged and pulled generally perpendicularly with respect to said base, said spine further comprising engaging means near its terminal end for engaging said body part of said anchor pad, whereby said spine when its engaging means is engaged to an anchor pad and pulled in its proximal direction may pull said anatomical wall outward while a trocar/cannula assembly is being inserted by said apparatus in the terminal direction of the spine through said wall.

21. Apparatus for inserting a trocar/cannula assembly through a wall of an anatomical cavity of a patient, comprising a housing, a spine having a longitudinal axis, the spine having proximal and terminal ends, the housing coupled to the spine for movement along said axis, holding means on the housing for holding a trocar/cannula, and drive means coupled to said housing and spine for driving said housing axially on said spine toward said terminal end thereby moving said housing and trocar/cannula from an initial position to a final position where said trocar/cannula is inserted through said wall of an anatomical cavity of a patient, said apparatus further comprising (a) an anchor pad which has a base securable to the outer surface of said anatomical wall and a body part adapted to be engaged and pulled generally perpendicularly with respect to said base, and (b) engaging means near said terminal end of said spine for engaging said body part of said anchor pad, whereby said apparatus when its engaging means is engaged to an anchor pad and pulled in its proximal direction may pull said anatomical wall outward while a trocar/cannula assembly is being inserted by said apparatus through said wall in the terminal direction of the spine.

22. Apparatus for inserting a trocar/cannula assembly through a wall of an anatomical cavity of a patient, comprising a spine having proximal and terminal ends, means for holding a trocar/cannula on said spine, drive means for driving said trocar/cannula axially on said spine toward said terminal end, thereby moving said trocar/cannula from an initial position to a final position where said trocar/cannula is inserted through said wall of an anatomical cavity of a patient, said apparatus further comprising (a) an anchor pad which has a base securable to the outer surface of said anatomical wall and a body part adapted to be engaged and pulled generally perpendicularly with respect to said base, and (b) engaging means near said terminal end of said spine for engaging said body part of said anchor pad, whereby said apparatus when its engaging means is engaged to an anchor pad and pulled in its proximal direction may pull said anatomical wall outward while a trocar/cannula assembly is being inserted by said apparatus through said wall in the terminal direction of the spine.

* * * * *